United States Patent [19]

Floyd, Jr. et al.

[11] Patent Number: 4,613,611

[45] Date of Patent: Sep. 23, 1986

[54] METHOD OF TREATING DIABETES MELLITUS USING ARYLGLYOXALS

[75] Inventors: Middleton B. Floyd, Jr., Suffern; Jo A. Goidl, Spring Valley, both of N.Y.

[73] Assignee: American Cyanamid Company, Stamford, Conn.

[21] Appl. No.: 542,099

[22] Filed: Oct. 14, 1983

[51] Int. Cl.⁴ .................. A61K 31/38; A61K 31/34
[52] U.S. Cl. ................... 514/443; 514/438; 514/448; 514/461; 514/469; 514/576; 514/577; 514/578; 514/679; 514/681; 514/682; 514/685; 514/688; 514/689

[58] Field of Search ............... 514/685, 682, 681, 679, 514/443, 438, 469, 461, 688, 689, 448, 576, 577, 578

[56] References Cited

U.S. PATENT DOCUMENTS

| | | | |
|---|---|---|---|
| 3,962,459 | 6/1976 | Kathawala | 514/685 |
| 4,474,809 | 10/1984 | Floyd et al. | 514/443 |
| 4,474,810 | 10/1984 | Floyd et al. | 514/443 |

Primary Examiner—Alan Siegel
Attorney, Agent, or Firm—Edward A. Conroy, Jr.

[57] ABSTRACT

A method of treating diabetes mellitus using arylglyoxals which are known compounds.

39 Claims, No Drawings

METHOD OF TREATING DIABETES MELLITUS USING ARYLGLYOXALS

BACKGROUND OF THE INVENTION

This invention relates to a method of treating diabetes mellitus using arylglyoxals and various hydrates and adducts formed from them. These compounds are either new compounds or are known in the art per se or are homologs or derivatives of compounds disclosed in the art. None of the compounds of this invention have any known pharmaceutical utility. The compounds of this invention are hypoglycemic agents capable of ameliorating diabetes mellitus in mammals by acting to simulate and/or potentiate the action of insulin. This invention further relates to pharmaceutical compositions for the utilization of these compounds in the treatment of diabetes mellitus. Further, this invention relates to the chemical synthesis of the compounds disclosed herein.

The disease diabetes mellitus is characterized by metabolic defects in the production and utilization of glucose which result in the failure to maintain appropriate blood sugar levels. The result of this defect is elevated blood glucose or hyperglycemia. Research on the treatment of diabetes has centered on attempts to normalize fasting and postprandial blood glucose levels. Treatments have included parenteral administration of exogenous insulin, oral administration of drugs, and dietary therapies.

Initially it was thought that hyperglycemia was simply the result of a deficiency in the supply of insulin, the principle hormone which controls glucose metabolism. As a result, research focused on the source of insulin production, the beta cells of the pancreas, and pharmaceutical agents were discovered which stimulated the production of insulin by the pancreas. Although it remains true that a deficiency of insulin does cause hyperglycemia it has now been recognized that other metabolic defects can be a major cause of elevated blood glucose.

In Type I diabetes, also called juvenile onset or insulin-dependent diabetes, insulin deficiency is indeed the cause of hyperglycemia. However, the majority of diabetics suffer from a form of the disease referred to as Type II diabetes, also called maturity onset or non-insulin dependent diabetes. A main characteristic displayed by Type II diabetics is insulin resistance or insulin insensitivity. Insulin resistance is a condition in which avaiable insulin, secreted by the pancreas and circulating in the blood stream, fails to stimulate sufficient glucose uptake and utilization in insulin-sensitive tissue. This inability of certain tissues including liver, muscle, and fat, whose metabolic machinery is normally sensitive to insulin, to utilize glucose efficiently or to control endogenous glucose synthesis and glycogenolysis, results in elevated blood glucose.

Compounds which stimulate and/or potentiate the biological action of insulin would be beneficial in the treatment of hyperglycemia resulting from mild to moderate insulin insufficiency or insulin insensitivity. A compound which would simulate or mimic insulin's action would correct both insulin deficiency and insulin resistance by its own insulin-like action. Further, a compound which would potentiate insulin's action would ameliorate insulin deficiency by rendering the small amount of insulin which is present more efficacious and would decrease insulin resistance by acting synergistically to make insulin more effective. Thus compounds which show insulin-like and/or insulin potentiating activity would be beneficial for the treatment of hyperglycemia occuring in Type I or Type II diabetes.

The compounds of the present invention simulate and potentiate the bioligical action of isulin. They simulate insulin's action at least in part by promoting the cellular uptake and metabolism of glucose in the absense of insulin. They potentiate insulin's action by exerting a synergistic effect on insulin action in the presence of sub-maximal concentrations of insulin. The exact mechanism by which the compounds of this invention should be construed as limited to any particular mechanism of action. Nonetheless, the compounds of this invention are useful for the treatment of hyperglycemia and diabetes in mammals.

BRIEF SUMMARY OF THE INVENTION

This invention is concerned with a method of treating diabetes mellitus with compounds which may be represented by the following structural formula:

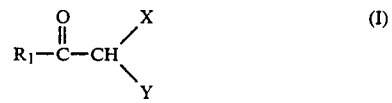

wherein $R_1$ is selected from the group consisting of 1-naphthyl, 2-naphthyl, 5-indanyl, 5,6,7,8-tetrahydro-2-naphthyl, 2-benzofuranyl, benzo[b]thiophene, 2,3,-dihydro-5-benzofuranyl, 4-benzyloxyphenyl, xanthenyl, o-terphenyl, 5-p-chlorophenyl-2-furanyl, phenylethoxyphenyl, mono- and di-substituted thiophene wherein the substituents are halogen or ($C_1$–$C_3$)-alkyl and mono- and poly-substituted phenyl wherein the substiuents are ($C_1$–$C_6$)alkyl, halogen or ($C_1$–$C_3$)-alkyl and mono- and poly-substituted phenyl wherein the substituents are ($C_1$–$C_6$)alkyl, halogen or trifluoromethyl; X and Y may be the same or different and are independently selected from the group consisting of hydroxy and —$SO_3Q$ wherein Q is an alkali metal or alkaline earth metal with the proviso that X and Y taken together may represent oxygen and the hydrates thereof.

In a more preferred embodiment, this invention is concerned with a method of treating diabetes mellitus with compounds represented by formula (I) wherein $R_1$ is selected from the group consisting of 1-naphthyl, 2-naphthyl, 5-indanyl, 5,6,7,8-tetrahydro-2-naphthyl, 2-benzofuranyl, benzo[b]thiophene, 2,3-dihydro-5-benzofuranyl, 4-benzyloxyphenyl, xanthenyl, o-terphenyl, 5-p-chlorophenyl-2-furanyl, phenylethoxyphenyl, mono- and di-substituted thiophene wherein the substituents are bromo, chloro or methyl, and mono- and poly-substituted phenyl wherein the substituents are chloro, bromo, fluoro, ($C_1$–$C_4$)alkyl or trifluoromethyl; X and Y may be the same or different and are independently selected from the group consisting of hydroxy and —$SO_3NA$ with the proviso that X and Y taken together may represent oxygen; and the hydrates thereof.

In a separate embodiment, this invention is concerned with new compounds which may be represented by the following structural formula:

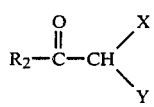

(II)

wherein $R_2$ is selected from the group consisting of xanthenyl, o-terphenyl, 5-p-chlorophenyl-2-furanyl, phenylethoxyphenyl, polyfluorophenyl, mono- and disubstituted thiophene wherein the substituents are chloro or methyl; and X and Y are as described for formula (I).

In as separate and preferred embodiment this invention is concerned with the following specific new compounds: α-hydroxy-β-oxo-xanthene-2-ethanesulfonic acid, sodium salt; dihydroxymethyl 2-xanthenyl ketone; α-hydroxy-β-oxo-o-terphenyl-4-ethanesulfonic acid, sodium salt; 2,5-dichloro-α-hydroxy-β-oxo-3-thiopheneethanesulfonic acid, sodium salt; 5-(p-chlorophenyl)-α-hydroxy-β-oxo-2-furanethanesulfonic acid, sodium salt; α-hydroxy-β-oxo-5-methyl-2-thiopheneethanesulfonic acid, sodium salt; 2,4-difluorobenzoylhydroxy-methanesulfonic acid, sodium salt; hydroxy(pentafluorophenyl)-methanesulfonic acid, sodium salt; and α-oxo-4-(2-phenylethoxy)-benzeneacetaldehyde.

This invention also relates to a method of treating hyperglycemia in a mammal in need of such treatment which comprises administering to said mammal an effective amount of a compound of formulae (I) or (II).

This invention also relates to a pharmaceutical composition which comprises an effective antidiabetic amount of a compound of formulae (I) or (II) in association with a pharmaceutically acceptable carrier.

This invention also relates to a pharmaceutical composition which comprises an effective hypoglycemic amount of a compound of formulae (I) or (II) in association with a pharmaceutically acceptable carrier.

Finally, this invention relates to processes for preparing compounds of formulae (I) or (II).

DETAILED DESCRIPTION OF THE INVENTION

Certain of the compounds of this invention may be prepared according to the following reaction sequence:

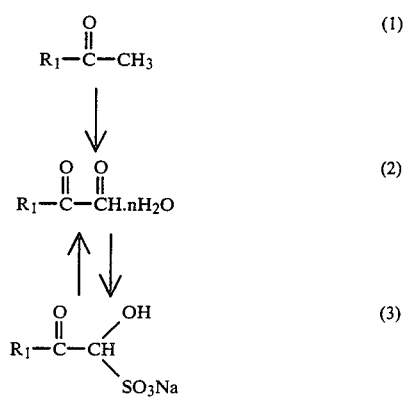

In accordance with the above reaction scheme, wherein $R_1$ is as hereinbefore defined, a ketone (1) is dissolved in dimethyl sulfoxide and treated with concentrated hydrobromic acid at 45°–65° C. for 18–48 hours. The reaction mixture is then poured onto ice and extracted with an organic solvent such as ethyl acetate. The extract is concentrated, dissolved in a mixture of ethanol and water at 50°–70° C. and treated with sodium metabisulfite at the boiling point for 5 minutes, then cooled under argon at 0° C., giving (3). The methanesulfonic acid, sodium salt derivative (3) is then suspended in water at 40°–60° C., acidified, heated at 90°–100° C. for 1–2 hours, cooled and extracted with diethyl ether. The ether extract is concentrated giving (2). Compounds of structure (2) are obtained in various degrees of hydration; that is, n may vary from almost zero to one or more. Alternatively, the ketone (1) is treated with selenium dioxide in aqueous dioxane at reflux, under an inert atmosphere, for 12–24 hours. The reaction mixture is then filtered and the filtrate evaporated, giving (2), which may be converted to the methanesulfonic acid, sodium salt derivative (3) by treatment with sodium metabisulfite in aqueous ethanol.

The compounds of this invention were tested for their insulin-like and insulin-potentiating activity according to the following procedure. Male, Wistar strain, Royal Hart rats weighing 125–170 g were sacrificed by decapitation. Their abdominal cavities were opened and distal or thin portions of epididymal fat pads excised, accumulated, and placed in 0.9% saline. The tissue was weighed and placed at a density of about 0.4 g/ml in Krebs-Henseleit bicarbonate (KNB) buffer containing 5 mg of crude bacterial collagenase per ml. [The KHB is composed of 118 mM sodium chloride; 4.7 mM potassium chloride; 1.2 mM calcium chloride; 1.2 mM potassium, dihydrogen phosphate; 1.2 mM magnesium sulfate heptahydrate; 25 mM sodium bicarbonate and 0.3 mM glucose and is saturated with oxygen: carbon dioxide (95:5).] The tissues were incubated with collagenase for one hour at 37° C. with gentle agitation in a Dubnoff metabolic shaker. At the end of this digestion period the cells were washed five times with twice their volume of KHB buffer containing fatty acid free bovine serum albumin (Pentex Fraction V) at a concentration of 3%. The digest was filtered through two layers of gauze and suspended in KHB buffer with albumin to a volume ten times the initial total weight of the fat pads. Incubation of one ml alimquots of the cell suspension was carried in the presence or absense of test compound and insulin. All tubes contained 0.15 uCi D-glucose-U-$^{14}$C. (specific activity 200 C/mmole).

Recrystallized porcine insulin (specific activity=25.5 U/mg) was dissolved in 0.9% saline adjusted to pH 3 with hydrochloric acid. The insulin was added to the cells at a concentration of approximately 5 uU.ml and control or basal cells received comparable volumes of pH 3 saline. Test compounds were dissolved in 50% dimethylsulfoxide-50% ethanol and added to the cells at a concentration of 100 μg/ml. Control cells received comparable volumes of dimethyl sulfoxide-ethanol.

After the tubes were loaded with insulin and test compound, or other vehicles, and cell suspension, they were capped with sleeve stoppers fitted with hanging, plastic center wells. Each well contained a small section of folded filter paper. The tubes were then gassed for about one minute with oxygen:carbon dioxide (95:5) via needles inserted through the septum of the stopper. Immediately after gassing, the radioactive glucose was injected into the incubate and the tubes were placed in a 37° C. metabolic shaking water bath and were incubated for one hour with gentle agitation.

At the end of the incubation, 0.4 ml of Hyamine hydroxide and then 0.5 ml of 5N sulfuric acid were carefully injected into the center well and cell suspension, respectively. The acidified cell suspension was then incubated an additional 30 minutes at room temperature with gentle agitation. At the end of this carbon dioxide collection period, the center wells were dropped into vials containing 10 ml of Dimiscint ® scintillation cocktail and the radioactivity counted by liquid scintillation spectrometry.

The measurement of carbon dioxide radioactivity in counts per minute produced by these cells in the absence of both test compound and insulin is the basal level (b). Radioactivity produced in the presence of test compounds only, insulin only and both test compound and insulin are (c), (i) and (ci), respectively. Each of (c), (i) and (ci) is then expressed as a percent of the basal value: C=c/b; I=i/b; CI=(ci)/b. Finally, insulin-like activity (%C/I) is calculated using the formula $$\% C/I = \frac{(100)(C - 100)}{(I - 100)};$$

and insulin-potentiating activity (%P) is calculated using the formula $$\% P = \frac{(100)(CI - C - I + 100)}{(I - 100)}.$$

The results of this test on representative compounds of this invention appear in Table I.

TABLE I

| Compound | % C/I | % P |
|---|---|---|
| 2,2-dihydroxy-2'-acetonaphthone | 464 | 27 |
| hydroxy-2-naphthoyl-methanesulfonic acid, sodium salt | 200 | 341 |
| hydroxy-1-naphthoyl-methanesulfonic acid, sodium salt | 183 | 171 |
| 2,2-dihydroxy-1'-acetonaphthone | 521 | 95 |
| 5-indanglyoxylaldehyde | 290 | 114 |
| 5,6,7,8-tetrahydro-2,2-dihydroxy-2'-acetonaphthone | 671 | 108 |
| α-hydroxy-β-oxo-2-benzofuranethanesulfonic acid, sodium salt | 192 | 80 |
| 2-benzofuranglyoxylaldehyde | 228 | 0 |
| 5,6,7,8-tetrahydro-α-hydroxy-β-oxo-2-naphthaleneethanesulfonic acid, sodium salt | 281 | 370 |
| 5-bromo-2-thiopheneglyoxylaldehyde | 255 | 64 |
| 5-bromo-α-hydroxy-β-oxo-2-thiopheneethanesulfonic acid, sodium salt | 82 | 70 |
| 2,4-dimethylbenzoylhydroxy-methanesulfonic acid, sodium salt | 108 | 99 |
| (3,4-dichlorophenyl)-glyoxal | 469 | 48 |
| hydroxy(3,4-dimethylbenzoyl)-methanesulfonic acid, sodium salt | 167 | 151 |
| (3,4-dichlorobenzoyl)-hydroxy-methanesulfonic acid, sodium salt | 65 | 124 |
| (2,5-dichlorobenzoyl)-hydroxy-methanesulfonic acid, sodium salt | 152 | 71 |
| m-bromobenzoylhydroxy-methanesulfonic acid, sodium salt | 328 | 181 |
| benzo[b]thiophene-3-glyoxylaldehyde | 135 | 13 |
| (p-tert-butylphenyl)-glyoxal | 900 | 0 |
| 3'-bromo-2,2-dihydroxy-acetophenone | 577 | 66 |
| 2,3-dihydro-5-benzofuranyl dihydroxymethyl ketone | 81 | 71 |
| hydroxy-p-toluoyl-methanesulfonic acid, sodium salt | 95 | 210 |
| p-tert-butylbenzoylhydroxy-methanesulfonic acid, sodium salt | 738 | 16 |
| 2,2-dihydroxy-4'-methyl-acetophenone | 169 | 180 |
| 2,2-dihydroxy-2',4'-dimethyl-acetophenone | 204 | 75 |
| 2,2-dihydroxy-4'-(trifluoromethyl)-acetophenone | 563 | 212 |
| hydroxy(α,α,α-trifluoro-p-toluoyl)-methanesulfonic acid, sodium salt | 578 | 387 |
| 4'-(benzyloxy)-2,2-dihydroxy-acetophenone | 802 | 220 |
| [p-(benzyloxy)benzoyl]hydroxy-methanesulfonic acid, sodium salt | 144 | 100 |

TABLE I-continued

| Compound | % C/I | % P |
|---|---|---|
| α-hydroxy-β-oxo-xanthene-2-ethanesulfonic acid, sodium salt | 125 | 0 |
| dihydroxymethyl 2-xanthenyl ketone | 151 | 0 |
| α-hydroxy-β-oxo-o-terphenyl-4-ethanesulfonic acid, sodium salt | 41 | 73 |
| 2,5-dichloro-α-hydroxy-β-oxo-3-thiopheneethanesulfonic acid, sodium salt | 234 | 176 |
| 5-(p-chlorophenyl)-α-hydroxy-β-oxo-2-furanethanesulfonic acid, sodium salt | 191 | 55 |
| α-hydroxy-β-oxo-5-methyl-2-thiopheneethanesulfonic acid, sodium salt | 162 | 55 |
| 2,4-difluorobenzoylhydroxy-methanesulfonic acid, sodium salt | 138 | 34 |
| hydroxy(pentafluorophenyl)-methanesulfonic acid, sodium salt | 220 | 0 |
| α-oxo-4-(2-phenylethoxy)-benzeneacetaldehyde | | |

When the compounds are employed for the above utility, they may be combined with one or more pharmaceutically acceptable carriers, e.g., solvents, diluents and the like, and may be adminstered orally in such forms as tablets, capsules, dispersible powders, granules, or suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 5 milligrams to about 100 milligrams per kilogram of animal body weight, preferably given in divided doses two to four times a day, or in sustained release form. For most large mammals, the total daily dosage is from about 500 milligrams to about 5,000 milligrams preferably from about 350 milligrams to 3,500 milligrams. Dosage forms suitble for internal use comprise from about 25 to 500 milligrams of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

4'-(Benzyloxy)-acetophenone

A mixture of 17.1 g of benzyl bromide, 13.6 g of 4-hydroxyacetophenone, 27.6 g of potassium carbonate and 200 ml of acetone was refluxed for 7 hours, then cooled and filtered. The filtrate was concentrated, then distilled on a Kugelrohr at 130°–140° C., 0.1 mm Hg. The oil was dissolved in acetone and then concentrated, giving the desired intermediate as a white solid, mp 92°–93° C.

EXAMPLE 2

Methyl 2-xanthenyl ketone

A 21.4 ml portion of acetyl chloride in 30 ml of 1,2-dichloroethane was added dropwise to 40 g of aluminum chloride in 105 ml of 1,2-dichloroethane. This mixture was stirred ½ hour and then added portionwise to an ice-cooled solution of 54.66 g of xanthene in 225 ml of 1,2-dichloroethane. The reaction was then allowed to warm to 16° C. and poured onto ice. A 180 ml portion of concentrated hydrochloric acid was added, the mixture was allowed to stand overnight and the layers separated. The aqueous layer was extracted with two 100 ml portions of chloroform then the organic layers was combined, dried, filtered through hydrous magnesium silicate and evaporated, giving the desired intermediate as a white crystalline solid, mp 103°–104° C.

Following essentially the procedures of Examples 1 or 2 and using appropriate starting materials, the intermediates of Examples 3–6, given in Table II were obtained.

TABLE II

| Example | Intermediate | Physical Constant |
|---|---|---|
| 3 | 4'-phenethyloxy-acetophenone | bp 110–120° C. |
| 4 | 3-acetylbenzothiophene | bp 104–110° C. |
| 5 | 2,3-dihydro-5-benzofuranyl methyl ketone | mp 55–57° C. |
| 6 | 2',4'-difluoro-acetophenone | bp 68–76° C. |

EXAMPLE 7

α-Oxo-4-(2-phenylethoxy)-benzeneacetaldehyde

A 27.7 g portion of 4'-phenethyloxy-acetophenone was dissolved in 200 ml of dimethylsulfoxide. A 39.2 ml portion of 48% hydrobromic acid was added in small portions (exothermic), then the mixture was heated at 58° C. for 17 hours. The mixture was poured into 500 ml of ice and water and the solid was collected, washed with water and dried, giving the desired product as a yellow solid, mp 44°–59° C.

EXAMPLE 8

2,2-Dihydroxy-2'-acetonaphthone

A mixture of 45.1 g of 2'-acetonaphthone, 29.4 g of selenium dioxide, 350 ml of dioxane and 7.0 ml of water was stirred, heated carefully to reflux and maintained at reflux for 3 hours. The mixture was cooled, filtered through diatomaceous earth and the filtrate evaporated in vacuo. The residue was treated with 300 ml of water and the resulting white solid collected and recrystallized from aqueous acetone giving the desired product as white crystals, mp 103°–120° C.

EXAMPLE 9

Hydroxy-2-naphthoyl-methanesulfonic acid, sodium salt

A stirred mixture of 10.1 g of 2,2-dihydroxy-2'-acetonaphthone, 5.7 g of sodium metabisulfite, 100 ml of water and 100 ml of ethanol was stirred overnight. The resulting solid was collected and washed successively with cold water, ethanol, acetone and ether, giving the desired product as an off-white solid, mp>210° C.

If desired, the dihydroxy analog may be regenerated by treatment of the above product with dilute mineral acid.

Following the essential procedures of Examples 7, 8 or 9 and using commercially available acetophenone derivatives, the intermediates of Examples 1–6, or intermediates derived by the procedures of Examples 1 or 2, the products of Examples 10–43 given in Table III were obtained.

TABLE III

| Example | Intermediate Derivation | Product | Physical Constant |
|---|---|---|---|
| 10 | 1'-acetonaphthone | 2,2-dihydroxy-1'-acetonaphthone | mp 76–86° C. |
| 11 | 10 | hydroxy-1-naphthoyl-methanesulfonic acid, sodium salt | mp 150–165° C. (dec.) |
| 12 | 6-acetyl-1,2,3,4-tetrahydronaphthalene | 5,6,7,8-tetrahydro-2,2-dihydroxy-2'-acetonaphthone | mp 97–101° C. |

TABLE III-continued

| Example | Intermediate Derivation | Product | Physical Constant |
|---|---|---|---|
| 13 | 12 | 5,6,7,8-tetrahydro-α-hydroxy-β-oxo-2-naphthaleneethanesulfonic acid, sodium salt | mp 182° C. (dec.) |
| 14 | 2-acetylbenzofuran | 2-benzofuranglyoxylaldehyde | mp 142–150° C. |
| 15 | 14 | α-hydroxy-β-oxo-2-benzofuranethanesulfonic acid, sodium salt | mp >200° C. |
| 16 | 2 | α-hydroxy-β-oxo-xanthene-2-ethanesulfonic acid, sodium salt | mp >300° C. |
| 17 | 2 | dihydroxymethyl 2-xanthenyl ketone | mp 123–125° C. |
| 18 | 4-acetyl-o-terphenyl | α-hydroxy-β-oxo-o-terphenyl-4-ethanesulfonic acid, sodium salt | mp 180° C. (dec.) |
| 19 | 2-acetyl-5-bromothiophene | 5-bromo-2-thiopheneglyoxylaldehyde | mp 113–115° C. |
| 20 | 19 | 5-bromo-α-hydroxy-β-oxo-2-thiopheneethanesulfonic acid, sodium salt | mp >300° C. |
| 21 | 3-acetyl-2,5-dichlorothiophene | 2,5-dichloro-α-hydroxy-β-oxo-3-thiopheneethanesulfonic acid, sodium salt | mp >210° C. |
| 22 | 2',4'-dimethylacetophenone | 2,4-dimethylbenzoylhydroxy-methanesulfonic acid, sodium salt | mp 167–171° C. |
| 23 | 22 | 2,2-dihydroxy-2',4'-dimethyl-acetophenone | |
| 24 | 3',4'-dichloroacetophenone | (3,4-dichlorophenyl)-glyoxal | mp 97–99° C. |
| 25 | 3',4'-dimethylacetophenone | hydroxy(3,4-dimethylbenzoyl)-methanesulfonic acid, sodium salt | |
| 26 | 3',4'-dichloroacetophenone | (3,4-dichlorobenzoyl)-hydroxy-methanesulfonic acid, sodium salt | |
| 27 | 2',5'-dichloroacetophenone | (2,5-dichlorobenzoyl)-hydroxy-methanesulfonic acid, sodium salt | |
| 28 | 3'-bromoacetophenone | m-bromobenzoylhydroxy-methanesulfonic acid, sodium salt | |
| 29 | 28 | 3'-bromo-2,2-dihydroxy-acetophenone | mp 112–115° C. |
| 30 | 4 | benzo[b]thiophene-3-glyoxylaldehyde | mp 120–126° C. |
| 31 | 4'-(tert-butyl)acetophenone | p-tert-butylbenzoylhydroxy-methanesulfonic acid, sodium salt | mp >300° C. |
| 32 | 31 | (p-tert-butylphenyl)-glyoxal | mp 105–109° C. |
| 33 | 2-acetyl-5-methylthiophene | α-hydroxy-β-oxo-5-methyl-2-thiopheneethanesulfonic acid, sodium salt | mp 180–195° C. (dec.) |
| 34 | 5 | 2,3-dihydro-5-benzofuranyl dihydroxymethyl ketone | mp 128–134° C. |
| 35 | 4'-methylacetophenone | hydroxy-p-toluoyl-methanesulfonic acid, sodium salt | |
| 36 | 35 | 2,2-dihydroxy-4'-methyl-acetophenone | mp 96–100° C. |
| 37 | 6 | 2,4-difluorobenzoylhydroxy-methanesulfonic acid, sodium salt | mp 184–190° C. |
| 38 | pentafluorobenzaldehyde | hydroxy(pentafluorophenyl)-methanesulfonic acid, sodium salt | |
| 39 | 4'-(trifluoromethyl)acetophenone | hydroxy(α,α,α-trifluoro-p-toluoyl)-methanesulfonic acid, sodium salt | |
| 40 | 39 | 2,2-dihydroxy-4'-(trifluoromethyl)-acetophenone | mp 85–87° C. |
| 41 | 1 | 4'-(benzyloxy)-2,2-dihydroxy-acetophenone | mp 93–98° C. |
| 42 | 41 | [p-(benzyloxy)benzoyl]hydroxy-methanesulfonic acid, sodium salt | |
| 43 | 5-(p-chlorophenyl)-2-furyl methyl ketone | 5-(p-chlorophenyl)-α-hydroxy-β-oxo-2-furanethanesulfonic acid, sodium salt | mp 200° C. |

EXAMPLE 44

5-Indanglyoxylaldehyde

5-Acetylindan was converted to α-hydroxy-β-oxo-5-indansulfonic acid, sodium salt by the procedures of Examples 8 and 9.

A warm solution of 5.1 g of this material in 50 ml of water was treated with 2.27 g of sodium bicarbonate on a steam bath for 15 minutes. The mixture was then cooled and 18 ml of 1N sodium hydroxide was added. The resulting oily precipitate was extracted into ethyl acetate. The organic extract was washed with water and brine, dried and evaporated to a yellow foam. This foam was triturated with ether, giving the desired product as off-white crystals, mp 100°–112° C.

We claim:

1. A method of treating diabetes mellitus in a mammal in need of such treatment which comprises administering to said mammal an effective amount of a compound selected from the group consisting of those of the formula:

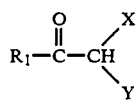

wherein $R_1$ is selected from the group consisting of 1-naphthyl, 2-naphthyl, 5-indanyl, 5,6,7,8-tetrahydro-2-naphthyl, 2-benzofuranyl, benzo[b]thiophene, 2,3-dihydro-5-benzofuranyl, xanthenyl, o-terphenyl, 5-p-chlorophenyl-2-furanyl, mono- and di-substituted thiophene wherein the substituents are halogen or (C$_1$–C-

3)alkyl; X and Y may be the same or different and are independently selected from the group consisting of hydroxy and —SO$_3$Q wherein Q is an alkali metal or alkaline earth metal with the proviso that X and Y taken together may represent oxygen; and the hydrates thereof.

2. A method of treating diabetes mellitus in a mammal in need of such treatment which comprises administering to said mammal an effective amount of a compound selected from the group consisting of those of the formula:

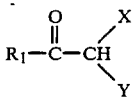

wherein R$_1$ is selected from the group consisting of 1-naphthyl, 2-naphthyl, 5-indanyl, 5,6,7,8-tetrahydro-2-naphthyl, 2-benzofuranyl, benzo[b]thiophene, 2,3-dihydro-5-benzofuranyl, xanthenyl, o-terphenyl, 5-p-chlorophenyl-2-furanyl, mono- and di-substituted thiophene wherein the substituents are bromo, chloro or methyl; X and Y may be the same or different and are independently selected from the group consisting of hydroxy and —SO$_3$Na with the proviso that X and Y taken together may represent oxygen; and the hydrates thereof.

3. A method of treating hyperglycemia in a mammal in need of such treatment which comprises administering to said mammal an effective amount of a compound selected from those of the formula:

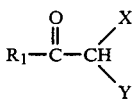

wherein R$_1$ is selected from the group consisting of 1-naphthyl, 2-naphthyl, 5-indanyl, 5,6,7,8-tetrahydro-2-naphthyl, 2-benzofuranyl, benzo[b]thiophene, 2,3-dihydro-5-benzofuranyl, xanthenyl, o-terphenyl, 5-p-chlorophenyl-2-furanyl, mono- and di-substituted thiophene wherein the substituents are halogen or (C$_1$-C$_3$)alkyl; X and Y may be the same or different and are independently selected from the group consisting of hydroxy and —SO$_3$Q wherein Q is an alkali metal or alkaline earth metal with the proviso that X and Y taken together may represent oxygen; and the hydrates thereof.

4. A method of treating hyperglycemia in a mammal in need of such treatment which comprises administering to said mammal an effective amount of a compound selected from those of the formula:

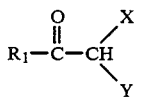

wherein R$_1$ is selected from the group consisting of 1-naphthyl, 2-naphthyl, 5-indanyl, 5,6,7,8-tetrahydro-2-naphthyl, 2-benzofuranyl, benzo[b]thiophene, 2,3-dihydro-5-benzofuranyl, xanthenyl, o-terphenyl, 5-p-chlorophenyl-2-furanyl, mono- and di-substituted thiophene wherein the substituents are bromo, chloro or methyl; X and Y may be the same or different and are independently selected from the group consisting of hydroxy and —SO$_3$Na with the proviso that X and Y taken together may represent oxygen; and the hydrates thereof.

5. A method according to claim 1 wherein the compound is 2,2-dihydroxy-2'-acetonaphtone.

6. A method according to claim 1 wherein the compound is hydroxy-2-naphthoyl-methane-sulfonic acid, sodium salt.

7. A method according to claim 1 wherein the compound is hydroxy-1-naphthoyl-methane-sulfonic acid, sodium salt.

8. A method according to claim 1 wherein the compound is 2,2-dihydroxy-1'-acetonaphthone.

9. A method according to claim 1 wherein the compound is 5-indanglyoxylaldehyde.

10. A method according to claim 1 wherein the compound is 5,6,7,8-tetrahydro-2,2-dihydroxy-2'-acetonaphthone.

11. A method according to claim 1 wherein the compound is α-hydroxy-β-oxo-2-benzofuranethanesulfonic acid, sodium salt.

12. A method according to claim 1 wherein the compound is 2-benzofuranglyoxylaldehyde.

13. A method according to claim 1 wherein the compound is 5,6,7,8-tetrahydro-α-hydroxy-β-oxo-2-naphthaleneethanesulfonic acid, sodium salt.

14. A method according to claim 1 wherein the compound is 5-bromo-2-thiopheneglyoxylaldehyde.

15. A method according to claim 1 wherein the compound is 5-bromo-α-hydroxy-β-oxo-2-thiopheneethanesulfonic acid, sodium salt.

16. A method according to claim 2 wherein the compound is 2,4-dimethylbenzoylhydroxy-methanesulfonic acid, sodium salt.

17. A method according to claim 2 wherein the compound is hydroxy(3,4-dimethylbenzoyl)-methanesulfonic acid, sodium salt.

18. A method according to claim 2 wherein the compound is (3,4-dichlorobenzoyl)-hydroxy-methanesulfonic acid, sodium salt.

19. A method according to claim 2 wherein the compound is (2,5-dichlorobenzoyl)-hydroxy-methanesulfonic acid, sodium salt.

20. A method according to claim 2 wherein the compound is m-bromobenzoylhydroxy-methanesulfonic acid, sodium salt.

21. A method according to claim 2 wherein the compound is benzo[b]thiophene-3-glyoxylaldehyde.

22. A method according to claim 2 wherein the compound is 3'-bromo-2,2-dihydroxy-acetophenone.

23. A method according to claim 3 wherein the compound is 2,3-dihydro-5-benzofuranyl dihydroxymethyl ketone.

24. A method according to claim 3 wherein the compound is hydroxy-p-toluoyl-methanesulfonic acid, sodium salt.

25. A method according to claim 3 wherein the compound is p-tert-butylbenzoylhydroxy-methanesulfonic acid, sodium salt.

26. A method according to claim 3 wherein the compound is 2,2-dihydroxy-4'-methyl-acetophenone.

27. A method according to claim 3 wherein the compound is 2,2-dihydroxy-2',4'-dimethylacetophenone.

28. A method according to claim 3 wherein the compound is 2,2-dihydroxy-4'-(trifluoromethyl)-acetophenone.

29. A method according to claim 3 wherein the compound is hydroxy(α,α,α-trifluoro-p-toluoyl)-methanesulfonic acid, sodium salt.

30. A method according to claim 3 wherein the compound is 4'-(benzyloxy)-2,2-dihydroxyacetophenone.

31. A method according to claim 3 wherein the compound is [p-(benzyloxy)benzoyl]hydroxy-methanesulfonic acid, sodium salt.

32. A method according to claim 3 wherein the compound is α-hydroxy-β-oxo-xanthene-2-ethanesulfonic acid, sodium salt.

33. A method according to claim 4 wherein the compound is dihydroxymethyl 2-xanthenyl ketone.

34. A method according to claim 4 wherein the compound is α-hydroxy-β-oxo-o-terphenyl-4-ethanesulfonic acid, sodium salt.

35. A method according to claim 4 wherein the compound is 2,5-dichloro-α-hydroxy-β-oxo-3-thiopheneethanesulfonic acid, sodium salt.

36. A method according to claim 4 wherein the compound is 5-(p-chlorophenyl)-α-hydroxy-β-oxo-2-furanethanesulfonic acid, sodium salt.

37. A method according to claim 4 wherein the compound is α-hydroxy-β-oxo-5-methyl-2-thiopheneethanesulfonic acid, sodium salt.

38. A method according to claim 4 wherein the compound is 2,4-difluorobenzoylhydroxy-methanesulfonic acid, sodium salt.

39. A method according to claim 4 wherein the compound is hydroxy(pentafluroophenyl)methanesulfonic acid, sodium salt.

* * * * *